US010479736B2

(12) United States Patent
Huntley, Jr.

(10) Patent No.: US 10,479,736 B2
(45) Date of Patent: Nov. 19, 2019

(54) METHOD FOR IMPROVING PLANT GROWTH BY IRRIGATION WITH NUTRIENTS

(71) Applicant: DIRT 2 SOIL LLC, Oceanside, CA (US)

(72) Inventor: Coleman Scott Huntley, Jr., Oceanside, CA (US)

(73) Assignee: Dirt 2 Soil LLC, Scottsdale, AZ (US)

( * ) Notice: Subject to any disclaimer, the term of this patent is extended or adjusted under 35 U.S.C. 154(b) by 0 days.

(21) Appl. No.: 16/184,672

(22) Filed: Nov. 8, 2018

(65) Prior Publication Data

US 2019/0077722 A1 Mar. 14, 2019

Related U.S. Application Data

(62) Division of application No. 15/522,283, filed as application No. PCT/US2015/057646 on Oct. 27, 2015, now abandoned.

(Continued)

(51) Int. Cl.
*C05F 17/02* (2006.01)
*A01N 63/00* (2006.01)
(Continued)

(52) U.S. Cl.
CPC .......... *C05F 17/0211* (2013.01); *A01C 21/00* (2013.01); *A01C 23/042* (2013.01);
(Continued)

(58) Field of Classification Search
CPC .......... A01N 63/00; C12N 1/20; A01C 21/00; A01C 23/042; C05F 11/08;
(Continued)

(56) References Cited

U.S. PATENT DOCUMENTS 3,685,656 A 8/1972 Schaefer
5,833,857 A 11/1998 Roth
(Continued)

FOREIGN PATENT DOCUMENTS

BR PI 1015504-0 A2 3/2014

OTHER PUBLICATIONS

International Search Report and Written Opinion issued by the International Searching Authority in International Patent Application No. PCT/US2015/057646 dated Jan. 27, 2016, 8 pages.
(Continued)

*Primary Examiner* — Gautam Prakash
(74) *Attorney, Agent, or Firm* — Jeffrey G. Sheldon; Kathrine B. Sales; Cislo & Thomas LLP

(57) ABSTRACT

A method of enhancing plant growth comprises a) selecting a mobile, self-contained system comprising a mobile structure, a vessel supported by the structure for receiving water and nutrients, a recirculating pump, a generator powering the pump, and a discharge line adapted for discharging contents of the vessel directly into an irrigation system; b) introducing into the vessel water and nutrient; c) moving the system; d) after moving, coupling the discharge line to an irrigation system or spray; and e) pumping the water and nutrient in the vessel with the pump out of the vessel through the discharge line directly into the irrigation system or spray.

13 Claims, 4 Drawing Sheets

Related U.S. Application Data

(60) Provisional application No. 62/069,068, filed on Oct. 27, 2014.

(51) Int. Cl.
    *C12N 1/20*     (2006.01)
    *A01C 21/00*     (2006.01)
    *A01C 23/04*     (2006.01)
    *C05F 11/08*     (2006.01)
    *C05F 17/00*     (2006.01)

(52) U.S. Cl.
    CPC ............. *A01N 63/00* (2013.01); *C05F 11/08* (2013.01); *C05F 17/0036* (2013.01); *C05F 17/027* (2013.01); *C05F 17/0276* (2013.01); *C12N 1/20* (2013.01); *Y02P 20/145* (2015.11); *Y02W 30/43* (2015.05)

(58) Field of Classification Search
    CPC ............ C05F 17/0211; C05F 17/027; C05F 17/0276; C05F 17/0036; Y02P 20/145; Y02W 30/43
    See application file for complete search history.

(56) References Cited

U.S. PATENT DOCUMENTS

| | | |
|---|---|---|
| 5,890,664 A | 4/1999 | Conant, III |
| 7,972,839 B2 | 7/2011 | Wilson |
| 2001/0052429 A1 | 12/2001 | Frenzel et al. |
| 2003/0113908 A1 | 6/2003 | Hussey, III et al. |
| 2007/0059819 A1 | 3/2007 | Storch |
| 2007/0186962 A1 | 8/2007 | Niedwiecki et al. |
| 2008/0210630 A1 | 9/2008 | Whiteman |
| 2009/0032446 A1 | 2/2009 | Wiemers et al. |
| 2011/0120945 A1 | 5/2011 | Kaya |
| 2014/0298717 A1* | 10/2014 | Ayers et al. ............. C12N 1/12 47/1.4 |

OTHER PUBLICATIONS

National Organic Standards Board Certification, Accreditation and Compliance Committee Recommendation to Allow Certified to USDA guidelines on Principal Display Panel of All Organic Labeling Categories (100% Organic, Organic and Made with Organic), Jul. 12, 2010, 6 pages.

U.S. Appl. No. 15/522,283, Requirement for Restriction dated Mar. 7, 2018.

U.S. Appl. No. 15/522,283, Non-Final Office Action dated May 4, 2018.

U.S. Appl. No. 15/522,283, Final Office Action dated Aug. 8, 2018.

U.S. Appl. No. 15/522,283, Advisory Action dated Oct. 16, 2018.

* cited by examiner

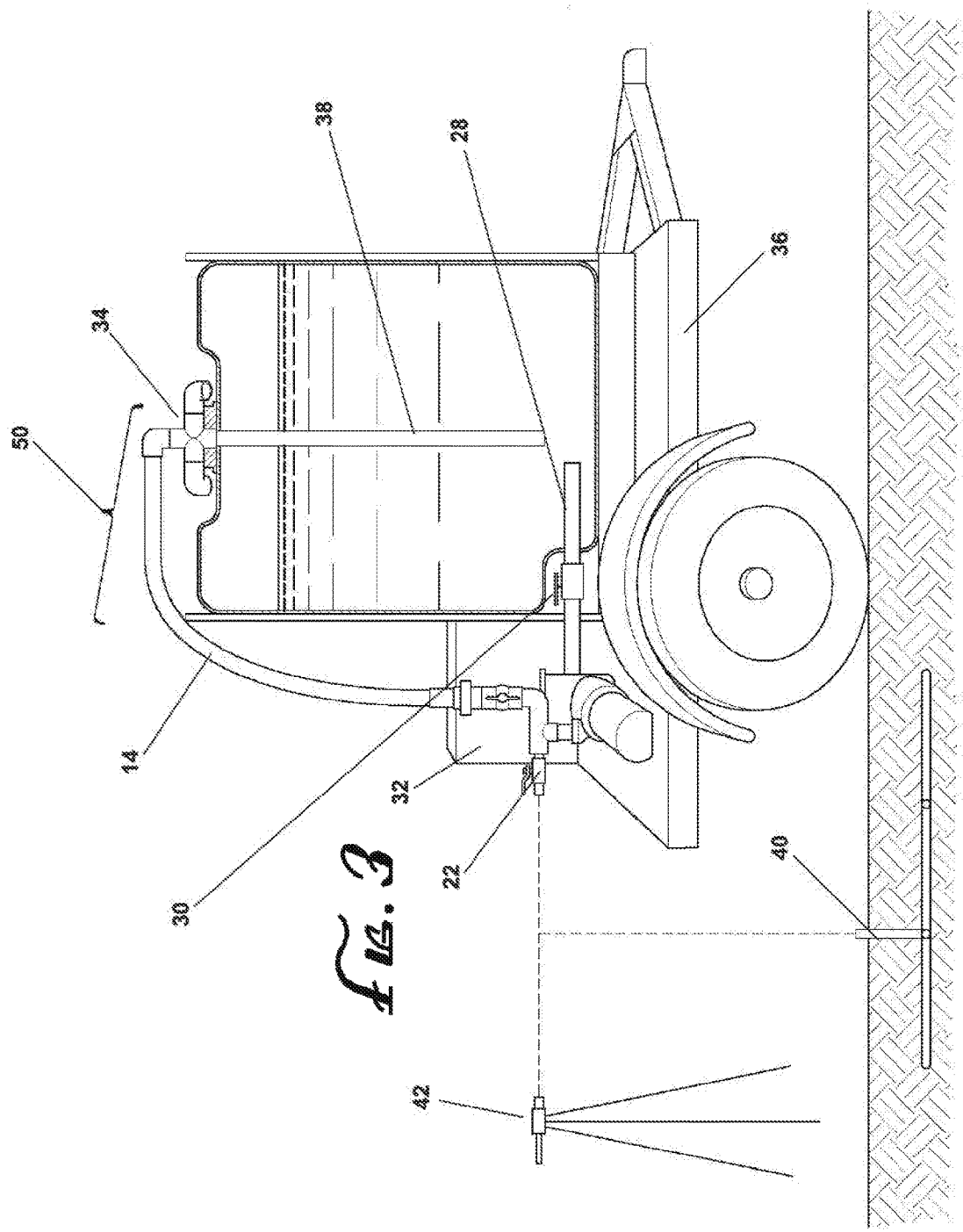

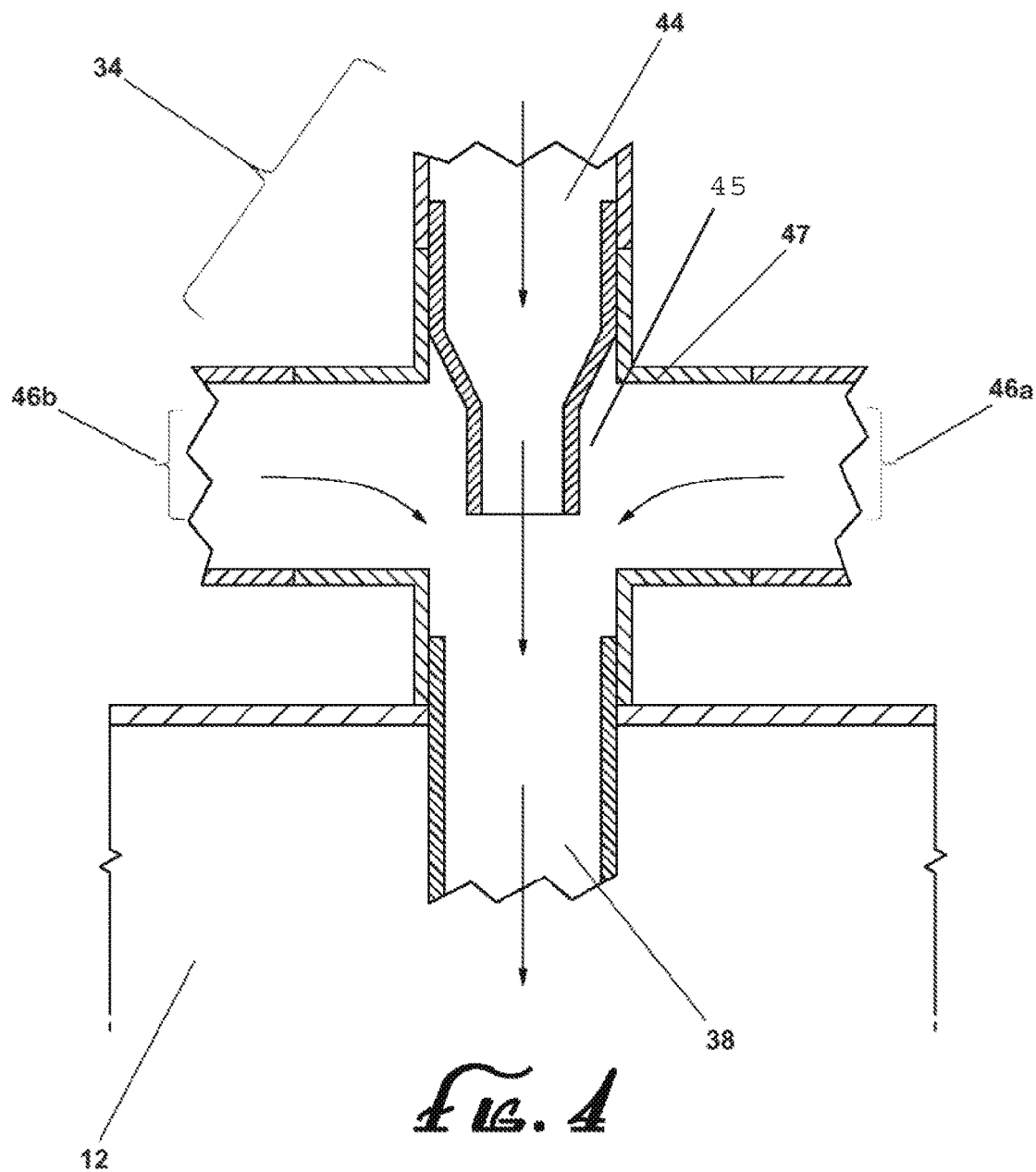

METHOD FOR IMPROVING PLANT GROWTH BY IRRIGATION WITH NUTRIENTS

CROSS-REFERENCE TO RELATED APPLICATION

This Application is a divisional application of U.S. Non-Provisional patent application Ser. No. 15/522,283, titled "A System for Enhancing Plant Growth," filed Apr. 26, 2017, which is a national stage of International Patent Application No. PCT/US2015/57646, titled "A System for Enhancing Plant Growth," filed Oct. 27, 2015, which claims the benefit of U.S. Provisional Patent Application No. 62/069,068 titled "Microorganism Brew System," filed Oct. 27, 2014, the contents of which are incorporated in this disclosure by reference in their entirety.

BACKGROUND

There is a need for organic, safe, inexpensive, natural aids for growing plants. Furthermore, there is a need for a single system that can deliver both organic and inorganic nutrients to plants and soil. Natural aids that contain beneficial microorganisms help prevent root and foliar diseases as well as adding nutrients to plants and soil. Such organic aids are becoming more recognized in commercial agriculture as a healthier alternative to pesticides and fertilizers.

Attempts to meet this need are described in U.S. patent application Ser. Nos. 10/024,854, 09/847,893, and 11/224,554 and U.S. Pat. No. 7,972,839. However, each of these attempts has deficiencies such as being bulky, expensive, immobile, and excessively complex.

Therefore there is a need for a system that overcomes the disadvantages of existing systems.

SUMMARY

The present invention is directed to a system suitable for enhancing plant growth that satisfies this need. The system is designed for both growing microorganisms and a method of administering the microorganisms as well as a system and method for delivering nutrients that do not need oxygen to grow. It provides a mobile brewery that is simple and efficient and can easily be administered via an irrigation system. Furthermore, this system utilizes an aerator to maintain a high level of dissolved oxygen continuously throughout the system.

In particular, the device comprises a mobile structure; a vessel supported by the structure for receiving water and nutrients; a pump supported by the structure and exterior to the vessel; a generator supported by the structure for powering the pump; a vessel outlet from a bottom portion of the vessel to the pump; a first discharge line from the pump extending from the pump into the bottom portion of the vessel, wherein the contents of the vessel can be circulated by the pump from the vessel outlet back into the vessel through the first discharge line; a second discharge line from the pump for discharging contents of the vessel; and an aerator for injecting air into the first discharge line for aerating the contents of the vessel. Furthermore, the aerator can be a venturi. The aerator can be removable to allow circulation of nutrients, such as inorganic nutrients, that do not require oxygen rich environments.

Optionally, the system can be provided with a power cord for providing AC power to the pump. The aerator can be disposed external and above the vessel for continuously aerating the solution as it is pumped through the aerator and back into the vessel. Furthermore, the first discharge line can comprise a first section from the pump to the top of the vessel and a second down section extending from the first section to the bottom portion of the vessel. Optionally, the second discharge line can be removed easily with a wrench, screw, or by hand. This allows changing out the second discharge line for injection into different pre-existing irrigation systems. For inorganic nutrients, optionally the aerator can be removable to allow use with microorganisms and nutrients that do not require oxygen.

In order to control the flow rate and direction of the solution each discharge line has a valve for selecting where the pumped contents of the vessel are discharged. Thus, the user can easily alternate the flow of the solution from continuous circulation to discharging onto plants.

The invention also includes a method for growing microorganisms and circulating nutrients for administering to plants. The method comprises the steps of adding water, microorganisms, and microorganism growth media into the vessel; circulating the contents with the pump by withdrawing contents of the vessel from the vessel outlet back into the vessel through the first discharge line, wherein air is sucked into the first discharge line by the venturi for aerating the contents of the vessel; cease pumping the contents of the vessel through the first discharge line; and pumping contents of the vessel with the pump out of the vessel through the second discharge line for enhancing the growth of plants. Another method requires that the aerator be removed before cycling the contents of the vessel.

Optionally, the user can move the vessel before pumping the contents out of the vessel. Furthermore, the user can optionally choose to attach the second discharge line to an irrigation system or a spray before pumping the contents of the vessel out. After discharging the contents of the vessel, the user can disconnect the vessel entirely from all other component parts for effective cleaning.

DRAWINGS

These and other features, aspects and advantages of the present invention will become better understood with regard to the following description, appended claims, and accompanying figures where:

FIG. 3 is a side view of the system of FIG. 1, partially in section; and

FIG. 4 is a sectional view of the aeration portion of the system of FIG. 1.

DESCRIPTION

Figure 1:
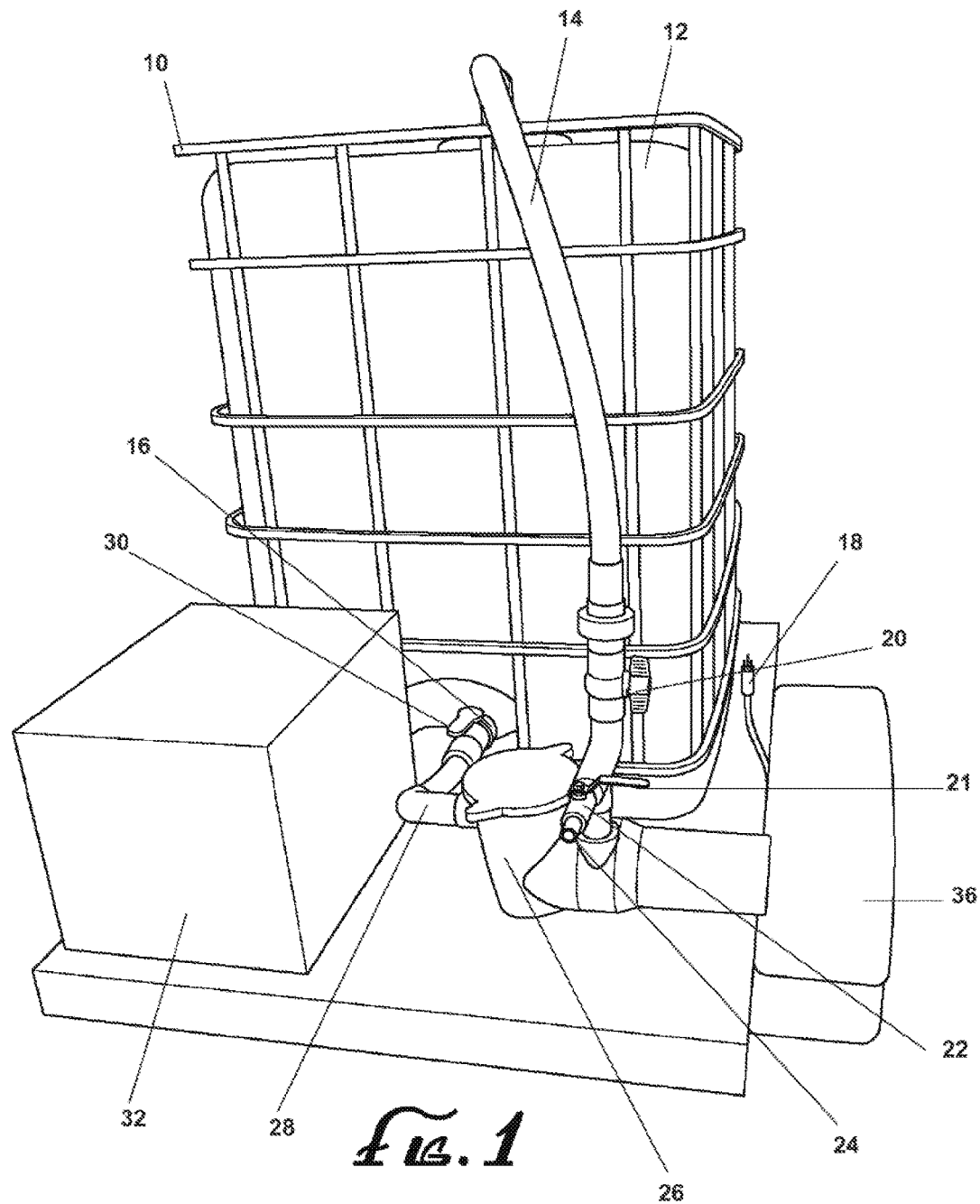
FIG. 1 is a front perspective view of a system having features of the present invention.

With reference to the figures, there is a system having features of the present invention comprising a mobile structure 36. The structure 36 can be towable or self-propelled. The structure supports the entire system including a vessel 12, a generator 32, a pump 26, piping, and a venturi 34 serving as an aerator.

Herein, the term "line" can refer to any structure capable of transporting a liquid, for example this could include a pipe. The term "pipe" is not meant to be exclusive but an example of one such "line" and can include other structures capable of transporting a liquid. The term "aerator" can comprise any structure capable of introducing air into the system; a venturi is one type of aerator.

Referring to FIGS. 1 and 3, the system provides for continual circulation and aeration of a microorganism solution. A mixture of microorganisms, nutrients, and water are contained within the vessel 12. The pump 26 extracts from the bottom of the vessel 12 the solution through a vessel outlet opening 16 and a vessel outlet pipe 28. A first discharge line 50 circulates the vessel contents. The first discharge line 50 can comprise a first section 14 from the pump to the top of the vessel and a second down section 38 extending from the first section 14 to the bottom portion of the vessel 12. The pump forces the solution up the first section 14 of the first discharge line 50 to a venturi 34 or aerator 34. As the solution passes through the venturi 34, the solution is aerated and forced back down into the vessel 12 via the second section 38 of the first discharge line 50. The system continues this circulation for the entire cultivation time until the solution is ready for application. This ensures continuous oxygen saturation and high quality and concentration of beneficial microorganisms. However, if the solution does not need to be aerated during the brewing or mixing process, the venturi 34 can be removed and the solution circulated with no aeration.

Referring to FIGS. 1 and 3, the system is designed for mobile as well as stationary brewing and application. The entire system is supported by a mobile structure 36. The mobile structure 36 can be towable or self-propelled. There is a generator 32 for powering the pump 26 where an AC power is not readily available. The generator 32 allows for the system to be fully mobile and can be administered easily at any location. Optionally, the system comprises a power cord 18 to power the pump 26 when AC power is easily accessible. Furthermore, the system comprises a second discharge line 22 for administering the contents of the vessel. The second discharge line 22 can be connected to an irrigation system 40 or can be attached to a spray 42 for mobile applications of the solution. Preferably, the pump is a diaphragm pump.

Any generator capable of powering such pump is envisioned. In one embodiment, the generator is a 4,000 watt portable PREDATOR™ generator.

The system is designed for ease of access and ease of cleaning. An important aspect of brewing these high-quality aids is cleanliness of the equipment. "Harmful" microbes can live in biofilm. Biofilm is the substance that builds up in, and remains in a brewing machine if it is not thoroughly cleaned after each brew. If the machine is not clean for subsequent brews, then the "harmful" microbes that remain in the biofilm can reproduce exponentially along with the "good" microbes and negatively affect the quality of the organic aid produced. The vessel 12 is modular so the vessel can be separated from the other components of the system for cleaning. The entire vessel 12 can be removed from the system, as it is lightweight and detachable. Therefore, the invention is a system that is easy to use and easy to clean, and that is economical and simple to operate.

Referring to FIG. 3, the vessel 12 is contained within a holding crate 10. The holding crate 10 can be any material or configuration suitable for holding and supporting the vessel 12 stationary such as but not limited to a skeleton, bolts, or even recessed notches. The holding crate 10 is easily moved in the field and can be connected easily to provide any total volume of solution required to irrigate any size field. Furthermore, multiple holding crates 10 with the vessel 12 can be used as slaves in order to provide a larger volume of solution for a greater surface area to be applied.

In this configuration multiple isolated units, each with its own pump and circulation system can be connected via piping or lines to one "master" second discharge line.

Figure 2:
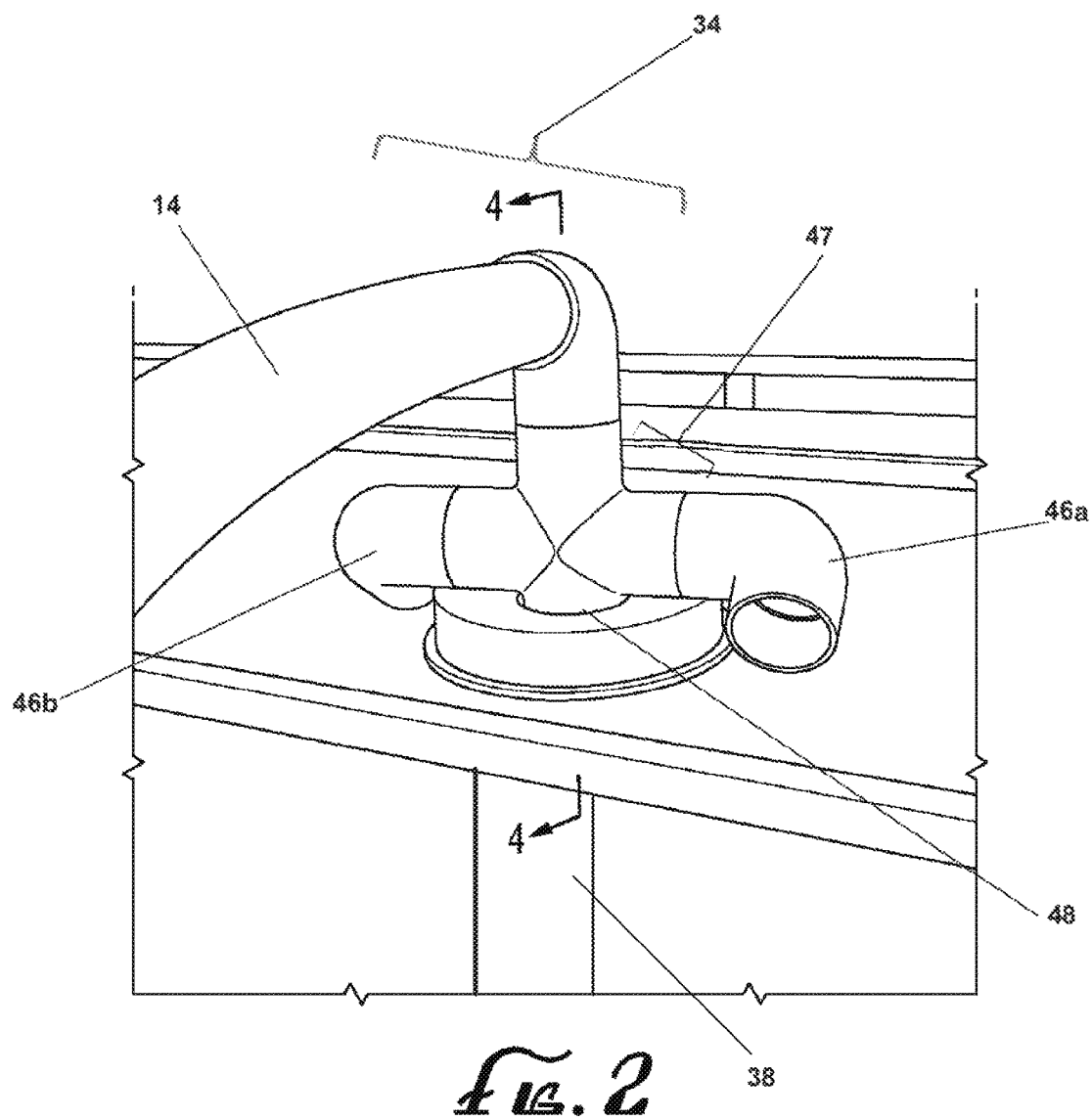
FIG. 2 is a perspective view of an aerating portion of the system of FIG. 1.

Only the vessel outlet pipe 28 and the second down section 38 of the first discharge line 50 are located interior to the vessel 12. However, both pipes can be easily removed and the vessel 12 completely removed for thorough cleaning. The pipes can be removed manually without tools or can require simple tools such as a screw and a wrench. Referring to FIG. 2, a "cross" 47 connects to the second down section 38 of the first discharge line 50 through an inlet 48 in the top of the vessel 12. Optionally, the "cross" 47 can be easily removed from the inlet 48 and the second down section of the first discharge line 50. Preferably, the second down section 38 of the first discharge line 50 is connected permanently to the cross 47 but can be easily removed with the cross intact. The second down section 38 of the first discharge line 50 is easily removed from the inlet 48 and thus removed from the vessel 12 for cleaning. This simple design allows the user to efficiently clean the vessel 12 to eliminate any residual biofilm in the vessel 12. Optionally, the bottom opening of the second down section 38 of the first discharge line 50 can have diffusers.

Referring to FIGS. 2 and 4, there is the venturi 34 that can provide optimum aeration of the liquid. Preferably, the venturi 34 maintains a continual minimum dissolved oxygen content of at least 6 ppm and typically up to 10 ppm. One configuration of an aerator, is the venturi 34. One configuration of the venturi 34 is comprised of the "cross" 47, two air/oxygen inlets 46*a/b*, a liquid inlet 45 and the descending second down section 38 of the first discharge line 50. The two oxygen inlets 46*a/b* are located opposite to each other and perpendicular to the flow of the liquid. Optionally, only one air inlet can be used. Liquid is pumped from the first section 14 of the first discharge line 50 to the top of the "cross" 47. As the liquid passes through the constricted pipe 44, creating a venturi effect, the two oxygen inlets 46*a/b* aerate the liquid. The aerated liquid is then pumped down the second down section 38 of the first discharge line 50 into the vessel 12. Furthermore, as seen in FIG. 3, the aerated liquid is forced down the second down section 38 of the first discharge line 50 to the bottom of the vessel 12 wherein the liquid "mushrooms" as it hits the flat surface of the bottom of the vessel and creates a swirling of the liquid similar to the motion of a washing machine. This process allows for uniform circulation throughout the vessel 12 as well as increasing the dissolved oxygen within the system.

The piping can be plastic or metal; the preferred piping is polyvinyl chloride.

It is desirable to control the flow rate and direction of the liquid. To accomplish this, the system comprises three valves: a vessel outlet valve 30 on the vessel outlet pipe 28 disposed between the pump 26 and the vessel 12, a first discharge valve 20 on the first section 14 of the first discharge line 50 disposed between the pump 26 and the "cross" 47, and a second discharge valve 21 on the second discharge line 22 disposed between the pump 26 and a barbed fitting 24 for attachment to an irrigation system. Using the valves, a user can alternate the direction and flow of the liquid from continuous circulation to the application on plants. For example, to maintain constant circulation, the pump 26 and generator 32 are turned on and first discharge valve 20 and vessel outlet valve 30 are opened while second discharge valve 21 is closed. Alternately, to discharge the contents of the vessel 12 while the pump 26 and generator 32 are on, second discharge valve 21 and vessel outlet valve 30 are opened while first discharge valve 20 is closed.

The water demand of the irrigation can vary during a typical irrigation cycle so it is desirable to measure the flow rate. This enables all of the water in the irrigation lines to be nutrient treated to assure even application of the nutrients to the medium. By varying the pressure output from the second discharge line 22 and diameter of the discharge pipes, the system can be adapted to any irrigation system and will precisely measure the dilution rate of the solution in the irrigation system and the flow of irrigation water.

Furthermore, it is desirable to be able to accommodate different irrigation systems of which can have different size piping and maximum and minimum pressure loads. This can be accomplished by varying the pressure output of the pump 26, varying the degree that the second discharge valve 21 is opened or closed in the second discharge line 22, or by varying the diameter of the piping in the second discharge line 22. In order to account for the varying pressures needed in different irrigation systems, it is preferred to use a diaphragm pump for pumping the solution. A diaphragm pump, such as a double diaphragm pump, provides the benefits, among others, of pumping chambers preventing the material being pumped to come in contact with any close fitting rotary or sliding seals to and capacities are infinitely variable within the pumps range. Because of the double diaphragm pump structure, it is ideal to be used with abrasives, slurries or even run dry. Therefore, there is no need to use variable speed motors or variable drives with a diaphragm pump.

EXAMPLE

Next, disclosed is the method of assembly of one embodiment of the invention. To create the venturi 34, take a 1.5 inch "bushing" and cut a "flange" off of the end (one quarter inch). Insert a 2.75 inch long 1 inch pvc pipe into the "bushing" so that it "seats" against the interior "flange" inside the "bushing" and hold in place in the center of the "cross" for one minute so that the glue dries. Insert the "bushing" into the "cross" 47 in the opposite direction that it was designed to be inserted so that the 2.75 inch long 1 inch pvc pipe extends into the center of the "cross" 47, leaving 0.5 inches of the (unglued) "bushing" outside the "cross" 47 so as to be accessible for inserting and gluing into a 1.5 inch "elbow". This leaves the 1 inch pvc pipe terminating in the middle of the "cross" 47 reducing the flow of liquid so as to create a venturi effect as the liquid passes through the "cross" 47 from top to bottom with the perpendicular "arms" of the cross serving as air inlets 46ab. Using a conical boring device, bore out the top of the "bushing" where it enters the "cross" 47 and reduces to 1 inch to enhance the venturi effect of the cross 47. This is now the top of the system.

Next, use two 2 inch lengths of pipe as "sleeves" and glue the (2) "arms" of the cross 47 to the "elbows" so that the opening of the "elbows" points down at a 30 degree angle. Glue the third "elbow" to the top of the "cross" 47 so that it is perpendicular to the arms of the "cross" where the "bushing" extends out 0.5 inch (over the venturi 34). Glue a 50 inch flexible pipe into the bottom arm of the "cross". This is now the second down section of the first discharge line 50 that inserts into the tank. Glue the flexible pipe into the "elbow" above the venturi. This is now the first discharge pipe 14. Glue the end of the flexible pvc pipe to the "union". This "union" will connect the flexible pipe to the valve 20 coming out of the pump.

Furthermore, the invention relates to a method for growing microorganisms and administering the microorganisms for enhancing the growth of plants using the systems of the invention. The method comprises adding water, microorganisms, and nutrients for the microorganisms into the vessel 12. Pumping to aerate the vessel 12 for a sufficient time to allow a majority of the microorganism to grow and develop. The contents of the vessel are circulated through the first section 14 of the first discharge line 50 to the liquid inlet 45, wherein air is sucked into the first discharge pipe 50 for aerating the contents of the vessel. Next, pump contents of the vessel 12 with the pump 26 out of the vessel for enhancing the growth of plants. The time required to circulate the contents of the vessel depends on the amount of solution and the area necessary to be irrigated in order to allow a majority of the microorganisms to fully develop.

Alternatively, microorganisms and nutrients can be circulated for administering to plants wherein the aerator 34 is removed before pumping to allow circulation without the introduction for air into the system.

One embodiment of the invention provides for the capacity to brew at between 200 and 600 gallons of solution, preferably at least 300 gallons. Depending on the bacteria desired and cultivation time, in one embodiment brewing generally takes about 2-4 hours. However, it is envisioned that less brewing time can be required. Preferably, the system is transported to the site of application and then brewed on site; however, brewing can take place anywhere as the system is mobile.

Optionally, the user can move the vessel 12 before pumping the contents out of the vessel 12. Furthermore, the user can optionally choose to attach the second discharge pipe 22 to an irrigation system 40 or a spray 42 before pumping the contents of the vessel. After discharging the contents of the vessel 12, the user can disconnect the vessel entirely from all other component parts for effective cleaning.

The microorganisms can comprise aerobic microbes consisting of archaea, bacteria, fungal hyphae, flagellates, amoebae, some ciliates, yeast cells and yeast fungal hyphae. The nutrient solution can be composed of any appropriate nutrients for such microorganisms, for example but not limited to black strap molasses, fish hydrolysate, and kelp meal. A product containing both microorganisms and nutrients is available from Simple Science LLC located in Salt Lake City, Utah, under the mark DIRT2SOIL.

Although the present invention has been described in considerable detail with reference to certain preferred versions thereof, other versions are possible. For example, different aerating means may be employed such as an air pump. Therefore, the spirit and scope of the appended claims should not be limited to the description of the preferred versions contained herein.

The invention claimed is:

1. A method for enhancing plant growth, the method comprising the steps of:
   a) selecting a mobile, self-contained system for enhancing plant growth comprising:
      i) a mobile structure comprising a plurality of wheels so that the system can be moved;
      ii) a vessel supported by the structure for receiving water and nutrients, wherein the vessel can contain up to 600 gallons of water;
      iii) a diaphragm pump supported by the structure and exterior to the vessel, the pump having a first discharge line and a second discharge line;
      iv) a generator supported by the structure for powering the pump;
      v) a vessel outlet from a bottom portion of the vessel to the pump; and vi) an aerator for injecting air into the first discharge line for aerating the contents of the vessel supported by the structure;

wherein the first discharge line extends from the pump directly into the bottom portion of the vessel, such that the contents of the vessel can be recirculated by the pump from the vessel outlet back into the vessel through the first discharge line and the second discharge line extends from the pump and is adapted for discharging contents of the vessel directly into an irrigation system, b) introducing into the vessel water and nutrient;

c) circulating the water and nutrient in the vessel with the pump by withdrawing the water and nutrient from the vessel through the vessel outlet, and pumping the withdrawn water and nutrient back into the vessel through the first discharge pipe, wherein air is sucked into the first discharge line by the aerator for aerating the water and nutrient in the vessel;

d) cease pumping the water and nutrient from the vessel through the #first discharge line;

e) moving the system;

f) after moving, coupling the second discharge line to an irrigation system or spray; and g) pumping the water and nutrient in the vessel with the pump out of the vessel through the second discharge line.

2. The method of claim 1, wherein the nutrient comprises inorganic nutrients.

3. The method of claim 1, wherein the vessel can contain from 200 up to 600 gallons of water.

4. The method of claim 1, where the pumping of step g) occurs with power provided by the generator.

5. The method of claim 1, wherein the nutrient comprises microorganisms and microorganism growth media.

6. The method of claim 5, wherein during step c), the microorganisms are growing.

7. A method of enhancing plant growth, the method comprising the steps of:
    a) selecting a mobile, self-contained system for enhancing plant growth comprising:
       i) a mobile structure comprising a plurality of wheels so that the system can be moved;
       ii) a vessel supported by the structure for receiving water and nutrients;
       iii) a recirculating pump supported by the structure and exterior to the vessel, the pump having a first discharge line and a second discharge line;
       iv) a generator supported by the structure for powering the pump;
       v) a vessel outlet from a bottom portion of the vessel to the pump; and
       vi) an aerator for injecting air into the first discharge line for aerating the contents of the vessel supported by the structure;
    wherein the first discharge line extends from the pump directly into the bottom portion of the vessel, such that the contents of the vessel can be recirculated by the pump from the vessel outlet back into the vessel through the first discharge line and the second discharge line extends from the pump and is adapted for discharging contents of the vessel directly into an irrigation system;
    b) introducing into the vessel water and nutrient;
    c) moving the system;
    d) after moving, coupling the second discharge line to an irrigation system or spray; and
    e) pumping the water and nutrient in the vessel with the pump out of the vessel through the second discharge line directly into the irrigation system or spray.

8. The method of claim 7, wherein the nutrient comprises inorganic nutrients.

9. The method of claim 7, wherein the nutrient comprises microorganisms and microorganism growth media.

10. The method of claim 7, where the pumping of step e) occurs with power provided by the generator.

11. The method of claim 7, wherein the recirculating pump is a diaphragm pump.

12. The method of claim 7, further comprising step f) after step b) circulating the water and nutrient in the vessel with the pump by withdrawing the water and nutrient from the vessel through the vessel outlet and pumping the withdrawn water and nutrient back into the vessel through the first discharge pipe, wherein air is sucked into the first discharge line by the aerator for aerating the water and nutrient in the vessel.

13. The method of claim 12, wherein the nutrient comprises microorganisms and microorganism growth media, and during step f), the microorganisms are growing.

* * * * *